(12) United States Patent
Schaefer et al.

(10) Patent No.: US 6,709,429 B1
(45) Date of Patent: Mar. 23, 2004

(54) INTRAVASCULAR CATHETER WITH MULTIPLE AXIAL FIBERS

(75) Inventors: Dean A. Schaefer, Roslindale, MA (US); David Paulk, Framingham, MA (US); Steven M. Anderson, Shrewsbury, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/487,353

(22) Filed: Jan. 19, 2000

(51) Int. Cl.[7] .......................... A61M 25/00; F16L 11/00
(52) U.S. Cl. .................... 604/527; 604/524; 604/526; 138/123
(58) Field of Search ................. 604/523, 524, 604/525, 526, 527, 529; 138/123, 129

(56) References Cited

U.S. PATENT DOCUMENTS

| | | | |
|---|---|---|---|
| 3,605,750 A | 9/1971 | Sheridan et al. | 128/348 |
| 4,063,561 A | 12/1977 | McKenna | 128/351 |
| 4,279,252 A | 7/1981 | Martin | 128/349 |
| 4,385,635 A | 5/1983 | Ruiz | 128/658 |
| 4,425,919 A | 1/1984 | Alston, Jr. et al. | 128/658 |
| 4,430,083 A | 2/1984 | Ganz et al. | 604/283 |
| 4,444,186 A | 4/1984 | Wolvek et al. | 128/325 |
| 4,464,176 A | 8/1984 | Wijayarathna | 604/164 |
| 4,469,483 A | 9/1984 | Becker et al. | 604/280 |
| 4,563,181 A | 1/1986 | Wijayarathna et al. | 604/280 |
| 4,571,240 A | 2/1986 | Samson et al. | 604/96 |
| 4,596,563 A | 6/1986 | Pande | 604/264 |
| 4,636,346 A | 1/1987 | Gold et al. | 264/139 |
| 4,657,024 A | 4/1987 | Coneys | 128/658 |
| 4,665,604 A | 5/1987 | Dubowik | 29/415 |
| 4,690,175 A | 9/1987 | Ouchi et al. | 138/131 |
| 4,741,087 A * | 5/1988 | Plummer, Jr. | 29/446 |
| 4,753,765 A | 6/1988 | Pande | 264/149 |
| 4,764,324 A | 8/1988 | Burnham | 264/103 |
| 4,817,613 A | 4/1989 | Jaraczewski et al. | 128/658 |
| 4,838,879 A | 6/1989 | Tanabe et al. | 604/280 |
| 4,842,590 A | 6/1989 | Tanabe et al. | 604/282 |
| 4,863,442 A | 9/1989 | DeMello et al. | 604/282 |
| 4,886,506 A | 12/1989 | Lovgren et al. | 604/280 |
| 4,898,591 A | 2/1990 | Jang et al. | 604/282 |
| 4,899,787 A | 2/1990 | Ouchi et al. | 138/131 |
| 4,904,431 A | 2/1990 | O'Maleki | |
| 4,925,710 A | 5/1990 | Buck et al. | 428/34.5 |
| 4,963,306 A | 10/1990 | Weldon | 264/101 |
| 4,990,143 A | 2/1991 | Sheridan | 604/282 |

(List continued on next page.)

OTHER PUBLICATIONS

U.S. patent application Ser. No. 09/234,203, Garabedian et al., filed Jan. 20, 1999.

*Primary Examiner*—Michael J. Hayes
*Assistant Examiner*—Lina R Kontos
(74) *Attorney, Agent, or Firm*—Crompton, Seager & Tufte, LLC

(57) ABSTRACT

An intravascular catheter having a shaft, at least a portion of which includes a braid reinforcement with a plurality of axial members disposed between the helical members that form the braid. The axial members provide a number of advantages including: maintaining one-to-one correspondence in axial manipulation; maintaining uniform flexibility in several planes of flexure; reducing the likelihood of causing a curling effect; increasing the strength of connections between shaft segments; uniformly increasing stiffness of the catheter; and increasing the burst strength of the catheter. By positioning the axial members between the helical members, the axial members do not create a protrusion and do not become fixed to any adjacent polymer layer. Thus, the benefits of axial members are retained, without creating the undesirable effects of friction caused by an axial protrusion and without creating the undesirable effects of limited flexure caused by an adjacent polymer layer becoming fixed to the axial member.

15 Claims, 1 Drawing Sheet

U.S. PATENT DOCUMENTS

| | | | |
|---|---|---|---|
| 5,019,057 A | 5/1991 | Truckai | 604/282 |
| 5,037,404 A | 8/1991 | Gold et al. | 604/282 |
| 5,045,072 A | 9/1991 | Castillo et al. | 604/280 |
| 5,057,092 A * | 10/1991 | Webster, Jr. | 138/123 |
| 5,061,257 A | 10/1991 | Martinez et al. | 604/282 |
| 5,078,702 A | 1/1992 | Pomeranz | 604/280 |
| 5,088,991 A | 2/1992 | Weldon | 604/280 |
| 5,156,785 A | 10/1992 | Zdrahala | 264/108 |
| 5,171,232 A | 12/1992 | Castillo et al. | 604/280 |
| 5,176,660 A * | 1/1993 | Truckai | 138/123 |
| 5,201,723 A | 4/1993 | Quinn | 604/264 |
| 5,221,270 A | 6/1993 | Parker | 604/282 |
| 5,234,416 A | 8/1993 | Macaulay et al. | 604/282 |
| 5,248,305 A | 9/1993 | Zdrahala | 604/280 |
| 5,254,107 A | 10/1993 | Soltesz | 604/282 |
| 5,290,230 A | 3/1994 | Ainsworth et al. | 604/96 |
| 5,300,048 A | 4/1994 | Drewes, Jr. et al. | 604/280 |
| 5,318,032 A | 6/1994 | Lonsbury et al. | 128/658 |
| 5,335,410 A | 8/1994 | Burnham | 29/452 |
| 5,380,304 A | 1/1995 | Parker | 604/282 |
| 5,399,164 A | 3/1995 | Snoke et al. | 604/95 |
| 5,403,292 A | 4/1995 | Ju | 604/282 |
| 5,433,713 A | 7/1995 | Trotta | 604/264 |
| 5,441,489 A | 8/1995 | Utsumi et al. | 604/280 |
| 5,445,624 A | 8/1995 | Jimenez | 604/280 |
| 5,451,209 A | 9/1995 | Ainsworth et al. | 604/96 |
| 5,454,795 A | 10/1995 | Samson | 604/282 |
| 5,499,973 A | 3/1996 | Saab | 604/96 |
| 5,509,910 A | 4/1996 | Lunn | 604/282 |
| 5,533,987 A | 7/1996 | Pray et al. | 604/280 |
| 5,538,510 A | 7/1996 | Fontirroche et al. | 604/265 |
| 5,540,707 A | 7/1996 | Ressemann et al. | 606/159 |
| 5,542,924 A | 8/1996 | Snoke et al. | 604/95 |
| 5,545,149 A | 8/1996 | Brin et al. | 604/265 |
| 5,582,619 A | 12/1996 | Ken | 606/191 |
| 5,584,821 A | 12/1996 | Hobbs et al. | 604/280 |
| 5,601,538 A | 2/1997 | Deem | 604/280 |
| 5,603,705 A | 2/1997 | Berg | 604/282 |
| 5,622,665 A | 4/1997 | Wang | 264/150 |
| 5,624,461 A | 4/1997 | Mariant | 606/191 |
| 5,658,263 A | 8/1997 | Dang et al. | 604/280 |
| 5,674,208 A | 10/1997 | Berg et al. | 604/282 |
| 5,676,659 A | 10/1997 | McGurk | 604/282 |
| 5,690,666 A | 11/1997 | Berenstein et al. | 606/191 |
| 5,702,373 A | 12/1997 | Samson | 604/282 |
| 5,718,711 A | 2/1998 | Berenstein et al. | 606/191 |
| 5,730,733 A * | 3/1998 | Mortier et al. | 604/527 |
| 5,749,891 A | 5/1998 | Ken et al. | 606/200 |
| 5,782,811 A | 7/1998 | Samson et al. | 604/282 |
| 5,817,057 A | 10/1998 | Berenstein et al. | 604/95 |
| 5,826,587 A | 10/1998 | Berenstein et al. | 128/898 |
| 5,827,201 A | 10/1998 | Samson et al. | 600/585 |
| 5,833,652 A | 11/1998 | Preissman et al. | 604/82 |
| 5,833,705 A | 11/1998 | Ken et al. | 606/191 |
| 5,853,418 A | 12/1998 | Ken et al. | 606/191 |
| 5,891,112 A | 4/1999 | Samson | 604/282 |
| 5,891,114 A | 4/1999 | Chien et al. | 604/282 |
| 5,895,391 A | 4/1999 | Farnholtz | 606/108 |
| 5,899,892 A | 5/1999 | Mortier et al. | 604/280 |
| 5,947,940 A | 9/1999 | Beisel | 604/282 |
| 6,152,909 A * | 11/2000 | Bagaoisan et al. | 604/173 |
| 6,171,295 B1 * | 1/2001 | Garabedian et al. | 604/264 |

* cited by examiner

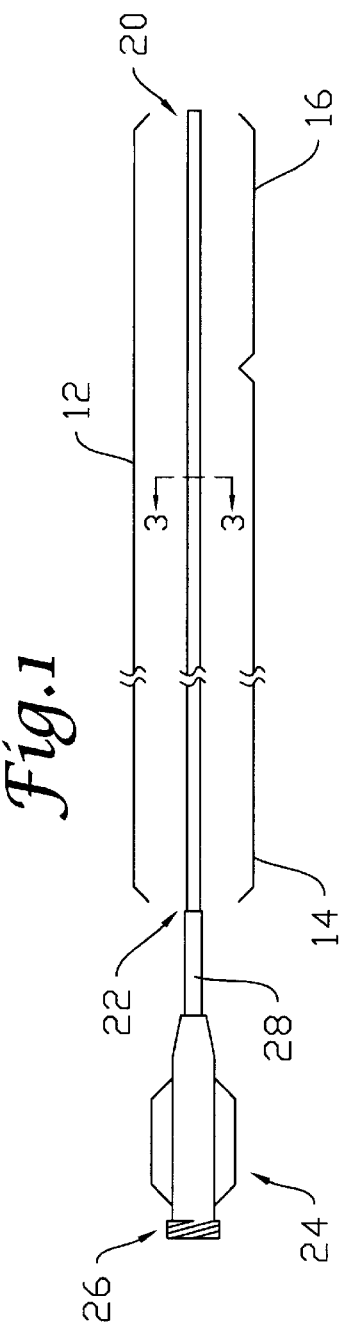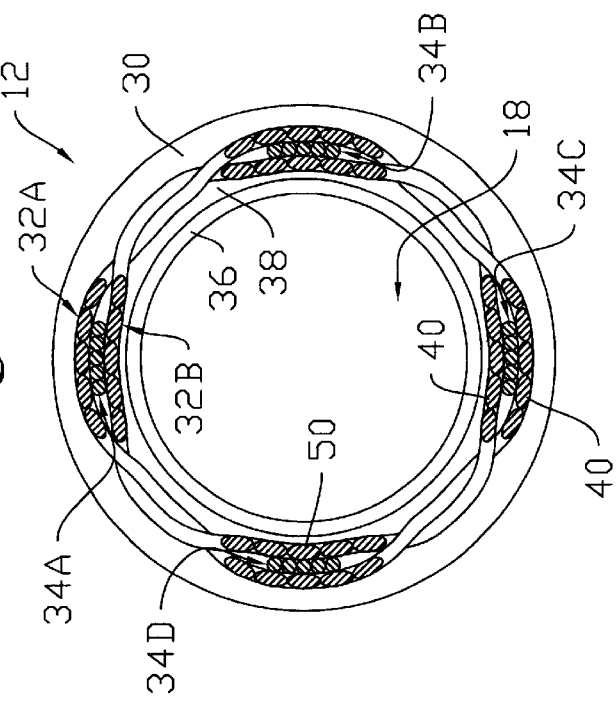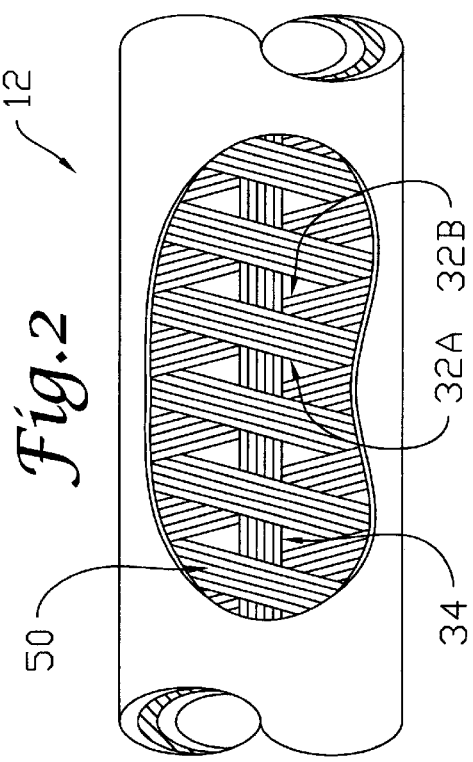

INTRAVASCULAR CATHETER WITH MULTIPLE AXIAL FIBERS

CROSS REFERENCE TO RELATED APPLICATIONS

The present invention is related to U.S. patent application Ser. No. 09/234,203, filed Jan. 20, 1999, entitled "INTRAVASCULAR CATHETER WITH COMPOSITE REINFORCEMENT"; now U.S. Pat. No. 6,171,295, issued Jan. 9, 2001; and U.S. patent application Ser. No. 09/487,359, filed on Jan. 19, 2000, entitled "INTRAVASCULAR CATHETER WITH AXIAL FIBER", the entire disclosures of which are hereby incorporated by reference.

FIELD OF THE INVENTION

The present invention generally relates to intravascular catheters. More specifically, the present invention relates to intravascular catheters having braid reinforcement.

BACKGROUND OF THE INVENTION

Intravascular catheters are used in a wide variety of relatively non-invasive medical procedures. Such intravascular catheters may be used for diagnostic or therapeutic purposes. Generally, an intravascular catheter allows a physician to remotely perform a medical procedure by inserting the catheter into the vascular system of the patient at a location that is easily accessible and thereafter navigating the catheter to the desired target site. By this method, virtually any target site in the patient's vascular system may be remotely accessed, including the coronary, cerebral, and peripheral vasculature.

The distance between the access site and the target site is often in excess of 100 cm. The inside diameter of the vasculature at the access site is often less than 2 cm, and the inside diameter of the vasculature at the target site is often less than 0.5 cm. Accordingly, intravascular catheters must be relatively long and thin. Furthermore, in order to navigate through the patient's tortuous vascular system, intravascular catheters must be very flexible. It is also desirable that intravascular catheters be relatively soft in order to minimize the probability of damaging vascular tissue.

Intravascular catheters typically have a radiopaque portion and are guided through the patient's vascular system with the assistance of x-ray fluoroscopy. A physician may manipulate the proximal end of the catheter and fluoroscopically monitor the corresponding movement of the distal end of the catheter. It is desirable that intravascular catheters be sufficiently radiopaque along their length and particularly at their distal end such that the physician is able to clearly monitor the progress of the catheter as it is being advanced from the vascular access site to the vascular target site.

After the intravascular catheter has been navigated through the patient's vascular system with the distal end thereof adjacent the target site, the catheter may be used for various diagnostic and/or therapeutic purposes. Frequently, diagnostic and therapeutic techniques require the infusion of fluids through the catheter. For example, it may be desirable to inject radiopaque contrast media through the catheter to provide enhanced fluoroscopic visualization for diagnostic purposes, or to inject pharmaceutical solutions (i.e., drugs) to the target site for therapeutic purposes. In order to maintain a fluid path, it is desirable that intravascular catheters be sufficiently resistant to kinking. In addition, because such fluids are delivered under pressure, it is also desirable that intravascular catheters be sufficiently resistant to bursting.

To satisfy some of these desirable features, prior art intravascular catheters have utilized a reinforcement structure such as a braid or coil disposed between an inner tubular polymer layer and an outer tubular polymer layer. A braid reinforcement structure may provide high resistance to bursting and improve the connection integrity between individual shaft segments. A coil reinforcement structure may provide adequate resistance to ovaling and kinking.

Some types of prior art intravascular catheters also utilize longitudinal or axial members to impart stiffness to the catheter shaft. For example, U.S. Pat. No. 5,057,092 to Webster discloses an intravascular catheter having a braid reinforcing mesh and longitudinal warp members. The longitudinal warp members are intended to provide increased bending stiffness and thus permit reductions in the wall thickness and/or softer materials for the inner and outer tubes. The warp members are interwoven with the braid such that warp members alternate under or over the braid mesh. Because the braid reinforcing mesh is disposed between an inner polymeric layer and an outer polymeric layer, portions of the longitudinal warp members are disposed between the braid reinforcing mesh and the adjacent polymeric layer.

With this arrangement, the adjacent polymeric layer may conform to the longitudinal warp members so as to create radial protrusions running the length of the catheter. A protrusion along the inside surface of the catheter may not be desirable because it may create friction or bias with devices inserted therein (e.g., guidewires). A protrusion along the outside surface of the catheter may not be desirable because it may create friction, bias or prevent adequate sealing with devices that the catheter is inserted into (e.g., introducer sheaths, compression fittings, etc.).

Also with this arrangement, the adjacent polymeric layer may become fixed to the longitudinal warp members as it conforms thereto. Fixing the longitudinal warp members to the adjacent polymeric layer may not be desirable because it may limit relative movement and flexure therebetween. Limiting relative movement and flexure may cause excessive stiffness in one or more planes of flexure. This may cause difficulties in manipulating and navigating the catheter through tortuous vasculature, which is clearly undesirable.

Accordingly, it is desirable to provide the advantages of a longitudinal or axial member without creating a protrusion and without fixing the axial member to the adjacent polymeric layer.

SUMMARY OF THE INVENTION

The present invention overcomes these disadvantages by providing an intravascular catheter that includes a braid reinforcement with a plurality of axial wires or fibers disposed between the helical members that form the braid. By placing the axial members between the helical members, the axial members do not create a protrusion on either side of the braid. In addition, the axial members do not become fixed to any polymer layer adjacent the braid. Thus, the present invention maintains the benefits of axial members, but without the undesirable effects of friction caused by an axial protrusion and without the undesirable effects of limited flexure caused by an adjacent polymer layer becoming fixed to the axial member.

In addition to avoiding the disadvantages discussed above by positioning the axial members between the helical members, the present invention provides several benefits by utilizing a plurality of axial members. First, the axial members prevent elongation of the shaft of the catheter thereby maintaining one-to-one correspondence in axial manipulation of the catheter, even when the shaft is placed in tension. Second, by equally spacing the axial members about the circumference of the catheter, the shaft maintains uniform flexibility in several planes of flexure thereby facilitating precise control of the catheter as it is navigated through tortuous vasculature. Third, as compared to a single axial member, uniformly spacing the axial members about the circumference of the catheter reduces the likelihood of causing the catheter to curl when the lumen of the catheter becomes clogged and the catheter is pressurized. Fourth, the strength of the connections between adjacent shaft segments is increased significantly. Fifth, the stiffness of the catheter may be uniformly increased thereby potentially reducing the profile of the catheter by allowing the wall thickness and/or hardness of the polymer layers to be reduced. Sixth, the burst strength of the catheter may be significantly increased by virtue of the axial members limiting radial expansion of the shaft.

An intravascular catheter in accordance with one embodiment of the present invention includes an elongate shaft having a lumen extending therethrough. The shaft includes an inner polymer layer, a reinforcement layer disposed about the inner layer and an outer polymer layer disposed about the reinforcement layer. The reinforcement layer comprises a tubular braid having two or more interwoven helical members. The reinforcement layer also includes a plurality of axial members disposed between the helical members such that the axial members are retained within the tubular braid structure for at least a length thereof. The axial members may be wires, fibers, filaments, cables or the like, but are generically referred to herein as axial members.

The axial members are preferably uniformly spaced about the circumference of the shaft. Virtually any number of axial members may be utilized, depending on the particular characteristics desired. For example, four or eight axial members may be utilized wherein the axial members are uniformly spaced apart by 90° or 45°, respectively, about the circumference of the shaft. In addition, only a portion of the shaft may include a plurality of axial members. For example, the distal shaft portion may have fewer axial members than the proximal shaft portion such that the distal shaft portion is more flexible.

The helical members that form the braid may each comprise polymeric material, a metallic material, or a combination thereof. Similarly, the axial members may comprise a polymeric material or a metallic material. If a polymeric material is utilized for the helical members or the axial members, then each member may comprise a plurality of monofilaments such as LCP. The monofilaments may be held together statically thereby eliminating the need for a binding material that might otherwise add to the profile of the members. To further minimize profile, the monofilaments may be arranged side-by-side to collectively define a flat ribbon or cable.

An intravascular catheter in accordance with another embodiment of the present invention includes an elongate shaft having a reinforcement layer. The reinforcement layer comprises a tubular braid including two or more interwoven helical members and a plurality of axial members disposed between the helical members. Optionally, the catheter may include inner and/or outer polymer layers disposed on either side of the reinforcement layer. Each of the inner and/or outer layers may comprise a single layer of polymeric material or multiple layers of polymeric materials.

The present invention also provides a method of making such a catheter. The manufacturing method includes the steps of braiding two or more helical members about a plurality of axial members such that the axial members are disposed between the helical members. The axial members are preferably uniformly spaced about the circumference of the shaft. The helical members may be braided over a carrier such as a mandrel that is later removed or a polymeric tubular member that becomes the inner layer of the catheter shaft. After the reinforcement layer is woven about the carrier, another polymeric tubular member may be disposed about the reinforcement layer to become the outer layer of the catheter shaft.

BRIEF DESCRIPTION OF THE DRAWINGS

FIG. 1 is a plan view of an intravascular catheter in accordance with the present invention;

FIG. 2 is fragmentary partially sectioned side view of the shaft of the catheter illustrated in FIG. 1; and FIG. 3 is a cross-sectional view taken along line 3—3 in FIG. 1.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

FIG. 1 illustrates intravascular catheter 10 in accordance with the present invention. Catheter 10 includes an elongate shaft 12 having a proximal region 14 and a distal region 16. The catheter 10 includes a lumen 18 (as best seen in FIG. 3) extending through the entire length of the elongate shaft 12 to an opening at the distal end 20 of the shaft 12. Catheter 10 may have, for example, a length of 80–150 cm and an outside diameter of approximately 3F.

A manifold 24 is connected to the proximal end 22 of the shaft 12 which includes an interior (not visible) in fluid communication with the lumen 18 of the elongate shaft 12. The manifold 24 includes a standard fitting 26 for connection to a fluid source such as a syringe. A strain relief 28 is disposed between the manifold 24 and the proximal end 22 of the shaft 12 in order to reduce the tendency of the shaft to kink therebetween. The proximal end 22 of the elongate shaft 12 may extend through the strain relief 28 for connection to the manifold 24. Alternatively, the distal end of the strain relief 28 may be connected to the proximal end 22 of the elongate shaft 12 with the proximal end of the strain relief 28 connected to the manifold 24.

With either arrangement, the intravascular catheter 10 provides a fluid path from the fitting 26 of the manifold 24 to the distal end 20 of the elongate shaft 12 by way of the interior (not visible) of the manifold 24 and the lumen 18 of the elongate shaft 12. Intravascular catheter 10 may be intravascularly navigated over a guide wire (not shown) and used to deliver diagnostic and/or therapeutic fluids to a desired vascular target site using conventional techniques.

Elongate shaft 12 includes a proximal region 14 and a distal region 16. The proximal region 14 is typically more stiff than the distal region 16 in order to provide more pushability for advancing the distal region 16. The distal region 16 is usually more flexible than the proximal region 14 to provide more trackability for navigating tortuous vasculature. A multi-layer construction may be used in either the proximal region 14 or both the proximal 14 and distal 16 regions, depending on the pushability, trackability, and other characteristics desired for each region.

The multi-layer construction is best seen in FIGS. 2 and 3. In FIG. 2, the outer layer 30 has been removed to expose the braid reinforcement layer 50 comprising helical members 32 (individually designated as 32A and 32B) and the axial members 34 (individually designated as 34A, 34B, 34C and 34D). The helical members 32 and the axial members 34 are each shown as a set of monofilaments 40, but may also comprise a single monofilament 40. The multi-layer construction includes the inner lubricious polymer layer 36 surrounded by the braid reinforcement layer 50 which, in turn, is surrounded by the outer layer 30. A tie layer 38 may be provided between the braid reinforcement layer 50 and the inner lubricious layer 36.

The inner layer 36 may be formed of a lubricious polymer such as PTFE or HDPE and preferably has a relatively thin wall to minimize profile. Inner layer 26 has an inside diameter sufficiently large to accommodate a conventional guidewire and to accommodate the delivery of fluids therethrough at a sufficient flow rate. For example, the inside diameter of the inner layer 36 may be approximately 0.027 inches and the wall thickness of the inner layer 36 may be approximately 0.0005 inches. The inner layer 36 may be formed, for example, by coating or extruding a lubricious polymer such as PTFE over a removable mandrel, or by using other known manufacturing techniques.

The tie layer 38 may be utilized to secure the helical members 32 to the inner lubricious layer 36. The tie layer 38 enhances the bond between the inner lubricious layer 36, the helical members 32, and the outer layer 30. Tie layer 38 also fills any micro-pores that may form in the inner layer 36 to thereby increase burst strength. Further, tie layer 38 maintains the position of the helical members 32 on the inner layer 36 during the manufacturing process. The thickness of the tie layer 38 may be approximately 0.0003 inches to reduce the corresponding increase in profile. An example of a suitable material for tie layer 38 is polyurethane, which may be coated onto the inner lubricious layer 36.

As seen in FIGS. 2 and 3, the helical members 32 are interwoven to form a tubular braid. For purposes of illustration, only two helical members 32A and 32B are shown. Those skilled in the art will recognize that the braided helical members 32 may vary in number, pattern, pick-count, etc., without departing from the scope of the present invention. The helical members 32 may comprise a polymeric material, a metallic material or a combination thereof. Polymeric helical members 32 provide superior flexibility and softness, metallic helical members 32 provide superior radiopacity and kink resistance, and a combination of polymeric and metallic helical members 32 provide all these attributes.

If metallic materials are utilized, the helical members 32 may comprise stainless steel, nickel-titanium alloy, or a highly radiopaque material such as gold, tungsten, iridium, or an alloy thereof. If a plurality of metallic helical members 32 are utilized, one or more of the metallic helical members 32 may comprise stainless steel to provide superior strength and one or more of the other metallic helical members 32 may comprise a highly radiopaque material to provide enhanced radiopacity. Although stainless steel provides higher radiopacity relative to most polymers, a more dense material such as those identified above are preferred for purposes of radiographic visualization. The metallic helical members 32 may have a rectangular cross-section or a circular cross-section, depending on the desired mechanical characteristics and the desired effect on profile. For example, metallic helical members 32 may have a circular cross-section with a diameter of approximately 0.0016 inches.

If polymeric materials are utilized, the helical members 32 may comprise a single monofilament 40 or a plurality of monofilaments 40 as shown. The plurality of monofilaments 40 may be unfused or fused together depending on the desired characteristics. Unfused monofilaments 40 may be held together statically thereby eliminating the need for a binding material that might otherwise add to the profile of the shaft 12. To further minimize profile, the monofilaments 40 may be arranged side-by-side to collectively define a flat ribbon or cable, as best seen in FIG. 3.

Fused monofilaments 40 provide the helical members 32 with mechanical characteristics similar to that of a solid rod. Unfused monofilaments 40 held together statically provide the helical members 32 with mechanical characteristics similar to that of a cable. A cable, as opposed to a solid rod, is more flexible and is able to withstand more fatigue from repeated bending. As such, helical members 32 comprising a plurality of monofilaments 40 held together statically provide a shaft 12 that is more flexible and more durable. These features are significant because the catheter 10 must be able to navigate tortuous vasculature and withstand harsh handling conditions.

The monofilaments 40 may be made of a liquid crystal polymer (LCP) available under the trade name VECTRAN. Each monofilament 40 may have a circular cross-section having a diameter of 0.0007 inches. Each helical member 32 may comprise two (2) to ten (10), and preferably five (5) monofilaments 40 which, as stated previously, may be fused or unfused. The monofilaments 40 are preferably unfused and arranged side-by-side to essentially define a flat cable or ribbon. It is possible, however, that the monofilaments 40 be arranged in any manner to collectively define any other desired geometry.

The axial members 34 are disposed between the helical members 32A and 32B. Axial members 34 may comprise any of the same or similar structures and materials as helical members 32. Preferably, each axial member 34 comprises a plurality of LCP monofilaments 40 arranged side-by-side as a flat cable as best seen in FIG. 3.

The axial members 34 limit elongation of the shaft 12 when the catheter 10 is placed in tension. The catheter 10 may be placed in tension when the catheter 10 is retracted in the proximal direction or withdrawn from a patient's vascular system and some resistance to movement is encountered. If the resistance to movement is encountered distal of the proximal end 22, the catheter shaft 12 is placed in tension. When significant tension is applied to the shaft 12, the axial members 34 limit elongation of the shaft. Further, the axial members 34 maintain one-to-one correspondence between axial manipulation of the proximal end 22 and axial movement of the distal end 20 of the shaft 12, even when the catheter 10 is placed in tension. By maintaining one-to-one correspondence in axial manipulation, the axial members 34 maintain precise control of the catheter 10.

Not only do the axial members 34 limit elongation of the shaft 12 and maintain precise control of the catheter 10, but by positioning the axial member 34 between the helical members 32A and 32B, the axial members 34 do not create a radial protrusion or become fixed to an adjacent polymer layer, both of which may create undesirable effects.

Specifically, if the axial members 34 were placed over or under the helical members 32, radial protrusions may extend along the length of the inner layer 36 or the outer layer 30.

Such protrusions along the inside surface of the catheter 10 may not be desirable because they may create friction or bias with devices inserted into the lumen 18. In addition, protrusions along the outside surface of the catheter 10 may not be desirable because they may create friction, bias, or prevent adequate sealing with devices that the catheter 10 is inserted into. By positioning the axial members 34 between the helical members 32A and 32B, no protrusions are formed thereby maintaining low friction and adequate sealing.

Further, if the axial members 34 were positioned under or over the helical members 32A and 32B, the inner layer 36 or the outer layer 30 may become fixed to the axial members 34, thereby limiting relative movement and flexure therebetween. Limiting relative movement and flexure may cause excessive stiffness in one or more planes of flexure. This may cause difficulties in manipulating and navigating the catheter 10 through tortuous vasculature. By positioning the axial members 34 between the helical members 32A and 32B, relative movement therebetween is permitted thereby maintaining some amount of flexibility.

In addition to preventing axial elongation of the shaft 12 thereby maintaining one-to-one correspondence and axial manipulation of the catheter 10, the axial members 34 provide a number of other advantages. By equally spacing the axial members 34 about the circumference of the shaft 12, the shaft 12 maintains uniform flexibility in several planes of flexure corresponding to the number of axial members used. The greater the number of axial members used, the greater number of planes of uniform flexibility. Uniform flexibility provides precise control of the catheter 10 as it is navigated through tortuous vasculature.

As compared to a single axial member, uniform spacing of the axial members 34 about the circumference of the shaft 12 also reduces the likelihood of causing the catheter to curl when the lumen 18 of the catheter 10 becomes clogged and the catheter 10 is pressurized. This may be encountered, for example, if the catheter 10 is utilized to deliver embolic material that unintentionally occludes the lumen 18. By reducing the likelihood of curling, the likelihood of causing trauma to the interior of the vessel wall is also reduced.

The axial members 34 also increase the strength of the connections between adjacent shaft segments and the burst strength of the shaft 12. The axial members further provide additional stiffness to the catheter shaft 12 such that the wall thickness and/or hardness of the polymer layers 30 and 36 may be reduced.

The outer layer 30 may be formed of any suitable polymer such as polyether block amide having a wall thickness of approximately 0.0025 inches. The outer layer 30 may be loaded with a radiopaque contrast material such as barium sulfate, preferably loaded at 30% by weight. The outer layer 30 may be formed by interrupted layer coextrusion (ILC) as described in U.S. Pat. No. 5,622,665 to Wang, which is hereby incorporated by reference. The outer layer 30 may include a proximal portion formed of a relatively high durometer polymer and a distal portion formed of a relatively low durometer polymer. For example, the proximal ILC portion may be formed of PEBAX™ 7233, which has a durometer of 72D and the distal ILC portion may be formed of PEBAX™ 3533 having a durometer of 35D. By virtue of the ILC process, the outer layer 30 gradually transitions from the relatively high durometer polymer to the relatively low durometer polymer, thereby gradually decreasing stiffness distally.

A radiopaque marker band (not shown) may be provided at the distal end 20 of the shaft 12. Such a radiopaque marker band may be formed of gold, tungsten, iridium, or an alloy thereof. The radiopaque marker band may be disposed over the braid 50 and encapsulated by the outer layer 30. The radiopaque marker may be swaged onto or adhesively secured to the braid layer 50. A radiopaque marker band facilitates radiographic visualization and navigation as discussed previously.

The catheter 10 may be manufactured by a number of suitable manufacturing processes including the process described hereinafter. The inner layer 36 and the tie layer 38 may be obtained prefabricated from a suitable vendor, such as H.V. Technologies, and provided as discrete tubes or on a spool as a continuous tube. The helical members 32 are then braided over a carrier (e.g., the tube comprising the inner layer 36 and tie layer 38) with the axial members 34 therebetween as described in greater detail hereinafter. The braided subassembly is subsequently cut to the desired length. A marker band is slid over the braid reinforcement layer 50 into position adjacent the distal end 20 of the elongate shaft 12. The outer layer 30 comprising a prefabricated ILC tube is slid over the braid reinforcement layer 50. A heat shrink tube (e.g., FEP) is then placed over the shaft 12 components and the composite subassembly is pulled through a heated die. The die is heated to 380°–430° F causing the components of the shaft 12 to be fused and compressed together by the combined heat and compressive radial force. The heat shrink tube is then removed, exposing the completed shaft 12 subassembly. The manifold 24 and the strain relief 28 are then attached to the proximal end 22 of the elongate shaft 12 using conventional techniques. The distal end 20 of the elongate shaft 12 is then trimmed to the desired length and a soft tip is thermally fused thereto. A lubricious coating is then applied to the exterior of the catheter shaft 12.

As mentioned above, the helical members 32 are braided over a carrier with the axial members 34 therebetween. Although braiding helical members is well known in the art, positioning axial members between the helical members requires some modification to conventional braiding machines. For example, a conventional Steeger braiding machine may be modified to incorporate individual bobbin carriers that deliver the axial members 34 through a horn gear shaft. The axial member 34 carriers are retrofitted onto the horn gear. With this arrangement, one of the helical member 32A carriers is allowed to pass under and the other helical member 32B carrier is allowed to pass over the axial members 34. The net result is a braid reinforcement structure 50 comprising two or more interwoven helical members 32, with axial members 34 disposed therebetween.

From the foregoing, it should be apparent to those skilled in the art that the present invention provides both a novel intravascular catheter 10 and a novel method of manufacture thereof. The catheter 10 comprises an elongate shaft 12 including a braid reinforcement 50 with axial members 34 disposed between helical members 32 that form the braid 50. By positioning the axial members 34 between the helical members 32, the axial members 34 do not create the undesirable effects of friction caused by radial protrusions and further do not create the undesirable effects of limited flexure caused by an adjacent polymer 30 or 36 becoming fixed to the axial members 34. The axial members provide a number of advantages including: maintaining one-to-one correspondence in axial manipulation; maintaining uniform flexibility in several planes of flexure; reducing the likelihood of causing a curling effect; increasing the strength of connections between shaft segments; uniformly increasing stiffness of the catheter; and increasing the burst strength of the catheter.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. An intravascular catheter comprising an elongate shaft having a lumen extending therethrough, the shaft including an inner polymer layer, a reinforcement layer disposed about the inner layer and an outer polymer layer disposed about the reinforcement layer, the reinforcement layer comprising a tubular braid having a first helical member interwoven with a second helical member and a plurality of axial members, wherein the elongate shaft has a circumference and wherein the axial members are spaced apart about the circumference of the shaft;

wherein the plurality of axial members are disposed between the first helical member and the second helical member, thereby forming a plurality of crossover points, and wherein the inner and outer layers have respective surfaces that are free of protrusions caused by the axial members.

2. An intravascular catheter as in claim 1, wherein at each crossover point one of the helical members passes over a given axial member while the other helical member passes under that axial member.

3. An intravascular catheter as in claim 1, wherein the axial members are uniformly spaced about the circumference of the shaft.

4. An intravascular catheter as in claim 3, wherein four axial members are uniformly spaced apart by 90° about the circumference of the shaft.

5. An intravascular catheter as in claim 3, wherein eight axial members are uniformly spaced apart by 45° about the circumference of the shaft.

6. An intravascular catheter as in claim 3, wherein the elongate shaft includes a proximal portion and a distal portion, and wherein the distal shaft portion has fewer axial members than the proximal shaft portion.

7. An intravascular catheter as in claim 6, wherein the proximal shaft portion has the plurality of axial members and the distal shaft portion has one axial member selected from the plurality of axial members.

8. An intravascular catheter as in claim 1, wherein the axial members are movable relative to the inner and outer layers.

9. An intravascular catheter as in claim 1, wherein the first and second helical members each comprise polymeric material.

10. An intravascular catheter as in claim 9, wherein the first and second helical members each comprise a plurality of monofilaments.

11. An intravascular catheter as in claim 1, wherein the axial members each comprise a polymeric material.

12. An intravascular catheter as in claim 11, wherein the axial members each comprise a plurality of polymeric monofilaments.

13. An intravascular catheter as in claim 12, wherein the monofilaments are held together statically.

14. An intravascular catheter as in claim 13, wherein the monofilaments comprise LCP.

15. An intravascular catheter as in claim 14, wherein the monofilaments are arranged side-by-side to collectively define a flat ribbon.

* * * * *